Figure 1:
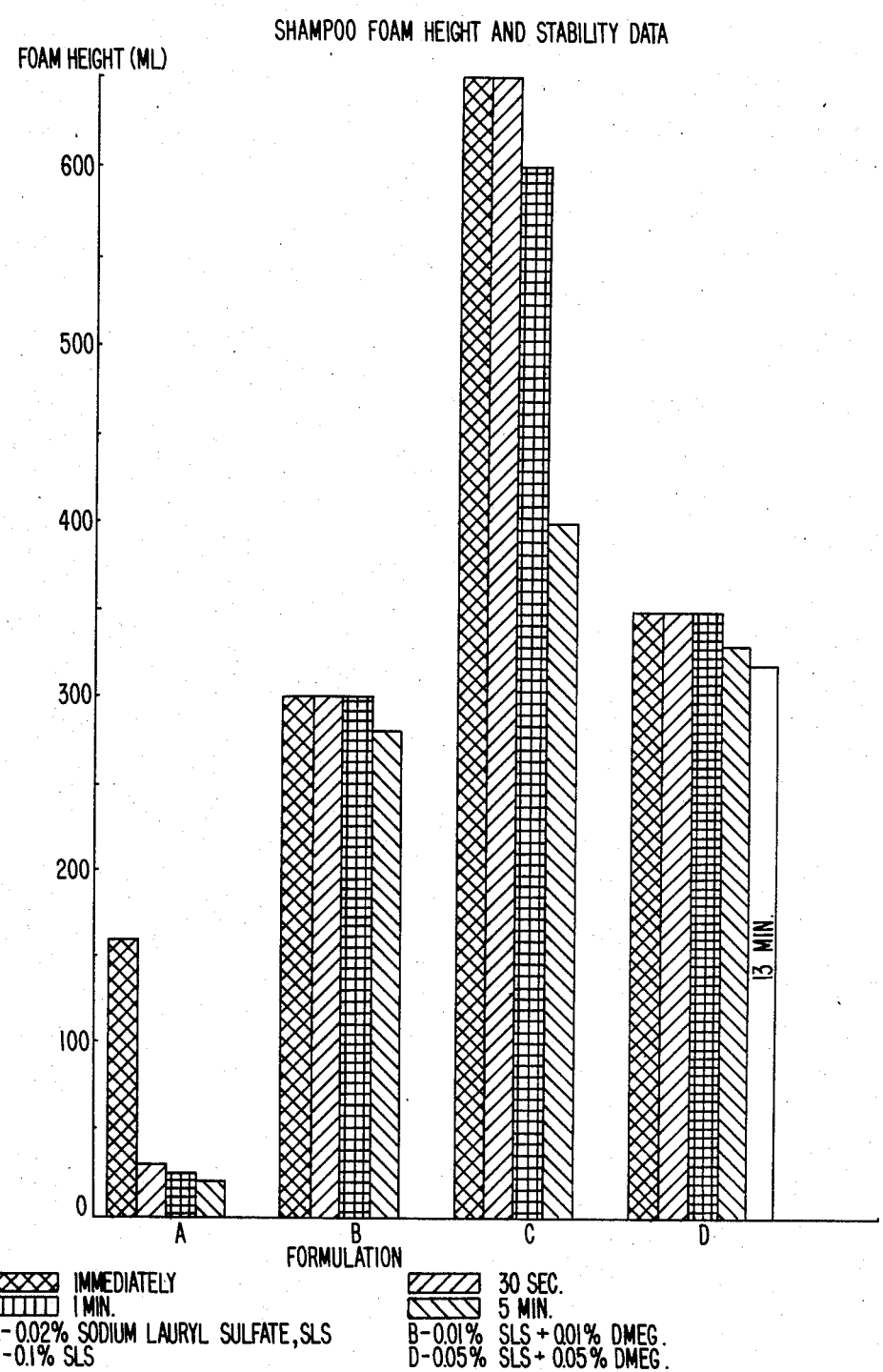

United States Patent [19]

Egan

[11] Patent Number: 4,663,444

[45] Date of Patent: May 5, 1987

[54] NON-IONIC CARBOHYDRATE BASED SURFACTANTS

[75] Inventor: Philip A. Egan, Meriden, Conn.

[73] Assignee: Olin Corporation, Cheshire, Conn.

[21] Appl. No.: 799,315

[22] Filed: Nov. 18, 1985

[51] Int. Cl.$^4$ ............................................. C07H 15/00
[52] U.S. Cl. ................................... 536/4.1; 536/18.6
[58] Field of Search ..................... 536/4.1, 18.5, 18.6

[56] References Cited

U.S. PATENT DOCUMENTS 4,454,123  6/1984  Noyori et al. ...................... 536/4.1

OTHER PUBLICATIONS

Migrdichian *Organic Synthesis,* Reinhold Publ. Corp., 1957, p. 76.
Liu et al., J. Am. Chem. Soc. (1982), vol. 104, p. 1178.
Chem. Abst., vol. 81, p. 1364054, Creasey et al. (1974).
Chem. Abst., vol. 82, p. 4531q, Machinami et al. (1975).
Chem. Abst., vol. 85, p. 193031x, Sinclair (1976).
Chem. Abst., vol. 88, p. 152920c, Ali Yousif et al. (1978).

*Primary Examiner*—Johnnie R. Brown
*Assistant Examiner*—Elli Peselev
*Attorney, Agent, or Firm*—William A. Simons; Thomas P. O'Day

[57] ABSTRACT

The present invention provides non-ionic carbohydrate based ethers having surfactant and other valuable properties of the formula:

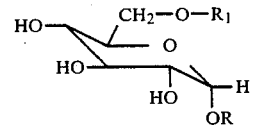

wherein: R is substituted or unsubstituted alkyl, aryl or aralkyl group containing 1-20 carbon atoms, and $R_1$ is an aryl, aralkyl, alkyl or alkenyl group containing 1-20 carbon atoms.

4 Claims, 2 Drawing Figures

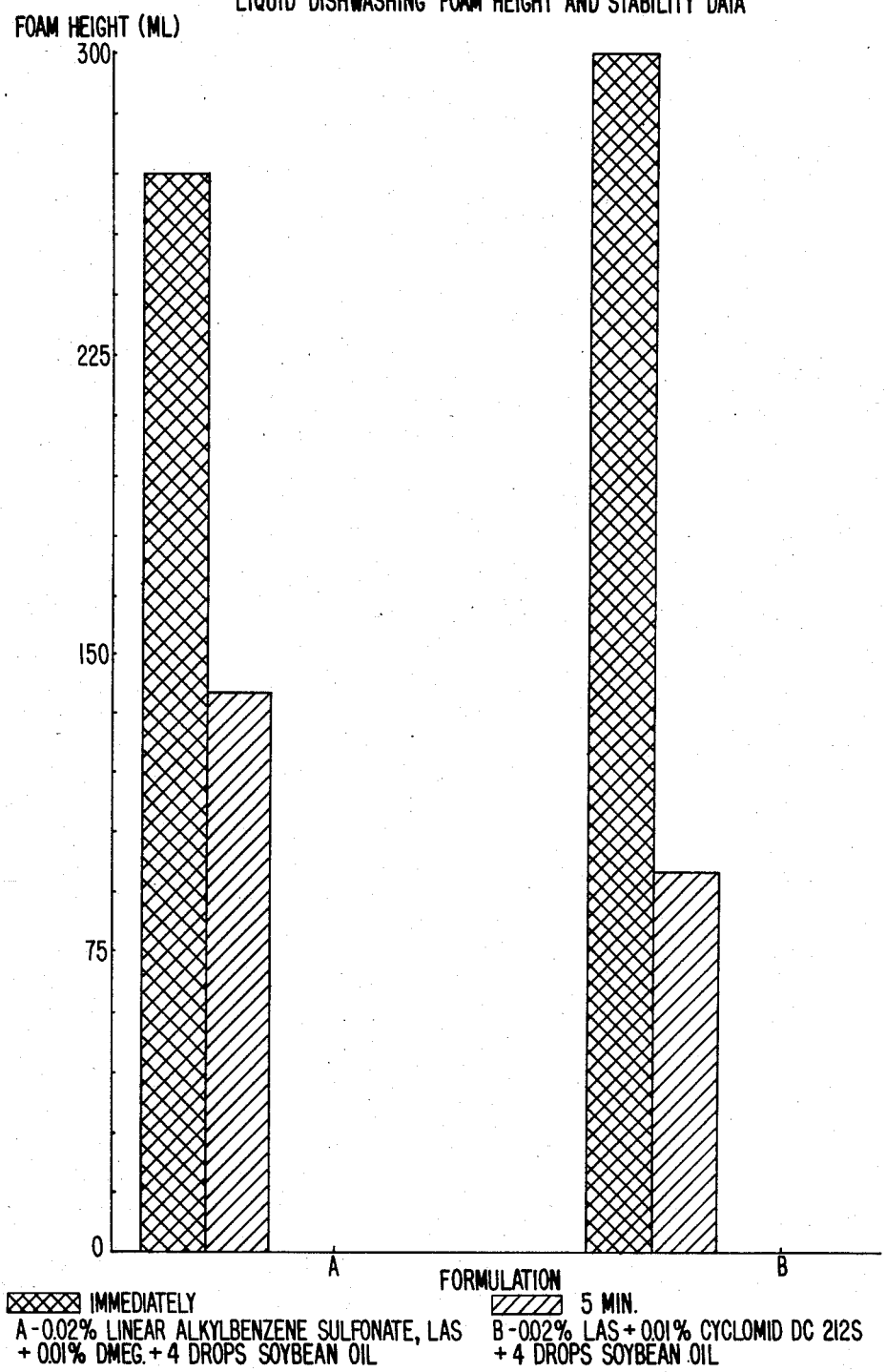

NON-IONIC CARBOHYDRATE BASED SURFACTANTS

BACKGROUND OF THE INVENTION

Most of the present day commercial non-ionic surfactants are prepared from petroleum or petroleum by-products. There exists an urgent need for non-ionic surfactants derived from natural sources such as carbohydrates since they offer numerous advantages. Thus, products derived from natural sources would offer a cost/performance advantage since present and future surfactant demands are dependent on formulation costs. In addition, carbohydrate-based surfactants would favorably impact critical environmental concerns such as nontoxicity and biodegradability. Moreover, carbohydrate surfactants offer raw material availability, relatively low costs and rejuvenitive capacity. All of these advantages would permit the efficient and inexpensive preparation of surfactants on a large-scale production basis.

The monomeric glucosides, e.g., methyl glucoside represent an attractive class of candidates for conversion to surfactants. Until the present time, the attachment of hydrophobic groups onto the methyl glucoside backbone required: (1) hydroxyl protection/deprotection steps, and/or (2) sequential transetherification, and/or (3) harsh or drastic reaction conditions using expensive metal hydrides. In all of these cases, the incompatibility of the materials resulting in the formation of a two-phase system made hydrophobic attachment difficult.

Methyl glucoside is prepared directly from hydrolyzed corn starch or glucose that has been treated with an acidic methanol solution according to the following equation:

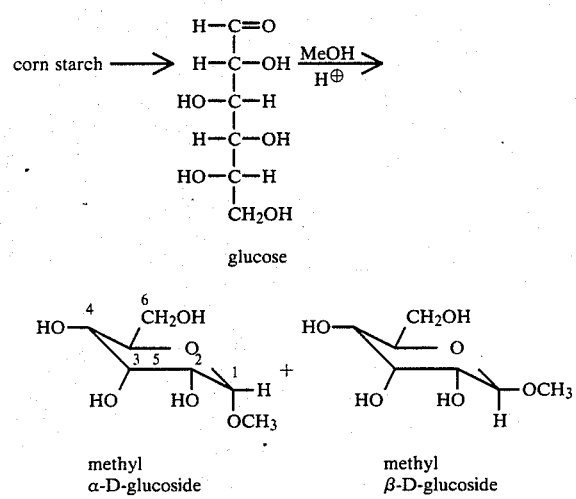

Generally, the α/β anomers are formed in the ratio of 2:1. Methyl glucoside is a non-reducing sugar which exists in the pyranoside or cylic form. Reducing sugars have unstable ring structures which are easily degraded under typical glucoside derivatization conditions. The methyl glucoside structure possesses four (4) potentially reactive hydroxyl sites at which various derivatives may be formed. The relative rectivities of these hydroxyl groups differ considerably as well as their contribution to the molecule's overall polarity. Typically, the primary hydroxyl center, located at carbon position No. 6, is favored followed by the secondary hydroxyl next to the methyl aglycon, carbon position No. 2.

The conventional method for attaching acid-stable, ether-linked hydrophobes onto a glucoside-based material is performed with a hydrophobic ($C_{12}$ or less) oxirane under basic conditions. Other methods include (1) addition of polymeric chains of lower oxyalkylene units (U.S. Pat. Nos. 2,407,002; 3,640,998; 4,264,478), (2) etherification of ethoxylated or propoxylated glucose (U.S. Pat. No. 3,737,426), (3) etherification of lipophilic glycosides (U.S. Pat. No. 4,011,389). In all cases, the reaction products are complex mixtures and contain acid labile hemiacetal or acetal linkages.

Acid sensitive linkages are also generated in other less commercially favorable glucoside hydrophobic attachment methods. These reactions are classified according to the following types: (1) alcoholysis with metal salts (Noller et al, J. Am. Chem. Soc., Vol. 60, p. 2076, 1938), (2) alcoholysis with acid catalysts (Wing et al, Carbohy. Res., Vol. 10, p. 441, 1969), and (3) transetherification (British Pat. No. 421,318). All of these reactions are multi-step, low yield, laborious processes which do not give well-defined products; thus, they have little practical commercial value. Regiochemical hydrophobic placement onto the glucoside molecule results in marked surface-active properties. Specifically, surfactant performance is improved by substitution on either the 3-O or 6-O position. The 6-O position is desirably etherified due to its easier accessibility.

It is an object of the present invention to provide novel and valuable non-ionic carbohydrate-based surfactants and a novel one-step, low temperature, high yield method for attaching hydrophobic groups to monomeric glucosides to form the non-ionic surfactants.

SUMMARY OF THE INVENTION

The present invention provides non-ionic carbohydrate based ethers having surfactant and other valuable properties of the formula:

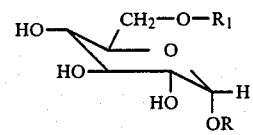

wherein: R is substituted or unsubstituted alkyl, aryl or aralkyl group containing 1-20 carbon atoms, and $R_1$ is an aryl, aralkyl, alkyl or alkenyl group containing 1-20 carbon atoms.

The present invention also provides a method for preparing the above-described ethers comprising:

(a) reacting, in the presence of a monovalent cation, a glucoside having the formula:

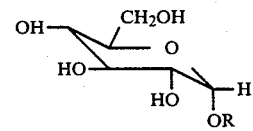

wherein: R has the meanings set forth above with a compound of the formula:

$R_1OSO_2CH_3$ wherein: R₁ has the meanings set forth above to produce an ether of of the formula:

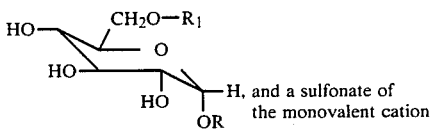

H, and a sulfonate of the monovalent cation

It will be understood by those skilled in the art that the invention includes the alternative embodiment wherein the glucoside may be reacted with a metallating agent to form the intermediate metal glucoside

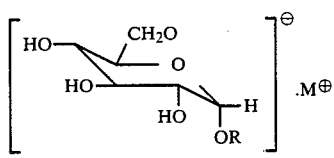

wherein: M is a monovalent metal ion, e.g., alkali metal, e.g., Na, K, and the like.

The methods for preparing the ethers of the invention are represented by the following reaction scheme wherein HO—(C₆H₁₀O₄)—CH₂—OH represents methyl glucoside.

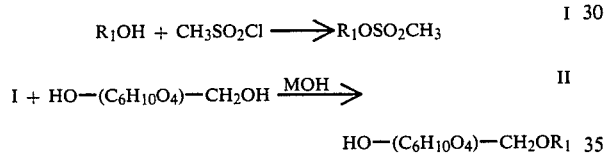

Wherein R₁ and M have the meanings set forth above.

The methods of the invention provide a novel route to an acid-insensitive, unambiguous, glucoside, nonionic surfactant product as outlined by the above reaction scheme. Since hydrophobic attachment is by an ether bond instead of an acetal linkage, the products are resistant to hydrolysis in both acid and basic media. Thus, the synthetic scheme involves high yielding (>85%) batch processes, thereby rendering it commercially attractive.

The first two steps involve a novel glucoside etherification route using linear mesylates as the alkylating agent. The intermediate mesylate (I) is prepared and isolated in >95% yield by the procedure of Crossland et al, J. Org. Chem. Vol. 35, p. 3195 (1970). This intermediate is then treated with a metal salt of the glucoiside at 50° for 24 hr. Any monovalent metal cation such as potassium or sodium may be used. Alkylation occurs predominantly at the primary hydroxyl position. The hydrophobic glucoside product (II) is isolated by simple extraction with, e.g., dichloromethane in >95% yield. No protection/deprotection or multi-step methods are required.

This methyl glucoside alkylation procedure is unprecedented, although 2-cellulose has been successfully alkylated with C₁₈ alkyl mesylates (copending U.S. patent application Ser. No. 629,516, filed July 10, 1984). Cellulosic chemical derivatization methods are not readily applicable to methyl glucoside systems due to the relative different molecular characteristics thereof. The latter system contains four (4) free hydroxyl groups which are strongly hydrogen bonded. Thus, cellulose electrophilic alkylation techniques are different or often prevented when applied to glucosides.

R may be any substituted or unsubstituted alkyl, aryl or aralkyl group such as methyl, ethyl, propyl, butyl, phenyl, benzyl or alkoxyphenol.

Particularly preferred are the unsubstituted straight or branched chain lower alkyl groups or aryl groups such as methyl, ethyl, propyl, butyl, phenyl, and the like, with methyl being the most preferred group. It will be understood by those skilled in the art that R may be any group which is substantially inert with respect to the method of synthesis of the derivatized glucoside.

EXAMPLE 1

Preparation of alkyl mesylates

The linear, alkyl alcohol (C₁₂-C₁₈, 0.15 mole) was added to dichloromethane (1250 mL) and triethylamine (50% excess). The mixture was mechanically stirred under a nitrogen atmosphere and cooled to −10° by a dry-ice/2-propanol slush bath. Mesityl chloride was added dropwise to the stirring reaction mixture over a 1 h. period. The reaction temperature was maintained at −10° and stirred for an additional hour. The resulting cold, milky-white, cloudy mixture was extracted sequentially with ice-cold: (1) ice-water, (2) 10% HCl, (3) saturated NaHCO₃, and (4) saturated sodium chloride.

The combined organic portions were dried over anhydrous MgSO₄. The products were isolated from the concentrated organic portion in 85% or 93% yield depending on the hydrocarbon chain (C₁₂-C₁₈).

The novel 6-O ether derivatives of the 1-O substituted glucosides (e.g., Example 1-b) are valuable nonionic, foam stabilizing agents. They substantially decrease the drainage rate of high foaming surfactants such as sodium laurylsulfonate and linear alkylbenzenesulfonate. Acid and base stability are imparted to the amphiphilic substances by an ether-linked hydrophobe onto the methyl-glucoside-hydrophilic moiety. Hydrophobic attachment occurs primarily at the methyl glucoside's primary hydroxyl group by a novel metal-glucoside attack on appropriate mesylates.

Carbohydrates are desirable as hydrophilic components of amphipathic materials because of their availability and rejuvenitive capacity. Nonionic surface-active agents derived from dextrose or other reducible carbohydrates are well known. [Shinoda et al, Bull. Chem. Soc. Japan (1961), Vol. 34, pp. 237–240; Shinoda et al, J. Phys. Chem. (1959), Vol.. 63, pp. 648–650; Noller et al, J. Am. Chem. Soc. (1938), Vol. 60, pp. 2076–2077; Bury et al, J. Trans. Faraday Soc. (1953), Vol. 49, pp. 209–211; Havlinova et al, Tenside Detergents, (1978), Vol. 15(2), pp. 72–74; Hughes et al, J. Am. Oil Chem. Soc. (1970), Vol. 47, pp. 162–167; Koeltzow et al, J. Am. Oil Chem. Soc. (1984), Vol. 61(10), pp. 1651–1655; Boettner, U.S. Pat. No. 3,219, 656 (1965); Boettner, British Pat. No. 1,072,655 (1967); Langdon, U.S. Pat. No. 4,011,389 (1977); Seldner, U.S. Pat. No. 4,264,478 (1981); Mansfield et al, U.S. Pat. No. 3,640,998 (1972); Mansfield et al, U.S. Pat. No. 3,547,828 (1970); Mansfield, U.S. Pat. No. 3,839,318 (1974); Throckmorton et al, U.S. Pat. No. 3,737,426 (1973); Bertsch et al, U.S. Pat. No. 2,049,758 (1936); Griffin, U.S. Pat. No. 2,407,002 (1946)]. These sugars contain a free aldehydic group which frequently, however, give colored and/or degraded product mixtures. Often, hydrophilicity is enhanced by alkylene oxide polymerization to yield polyoxylene alcohols.

Fatty-acid esters or acetal-linked high molecular weight linear alcohols usually provide the hydrophobic portion of the molecule. As a result, the materials are unstable in mildly alkaline or acidic media. In addition, they have limited solubility in moderately strong electrolyte solutions.

Ether-linked hydrophobes are intrinsically far more acid and alkali stable than esters or acetals. Previous synthetic hydrophobic attachment schemes are classified into five major categories (Table 1). In all cases, except for reaction type 4, ambiguous heterogeneous glycosidic mixtures are obtained. Typically, these product mixtures contain (1) unreacted D-glucose, (2) unreacted alcohol, and (3) polymeric materials. Moreover, D-glucose, or a unit thereof, must be present in order for these reactions to continue. In marked contrast, the present invention provides non-ionic, homogeneous surface-active molecules which contain the hydrophobic species attached to one or more sugar hydroxyls.

TABLE 1

| Type | Classification | Reaction Type | Linkage Type |
|---|---|---|---|
| 1 | Fischer Type | Glucose + ROH + acid catalyst | Acetal |
| 2 | Koenigs/Knorr | Acetohalogenglucose ROH + Ag$_2$CO$_3$ | Acetal |
| 3 | Transacetalization | Glucoside + ROH + acid catalyst | Acetal |
| 4 | Enzymatic | | Acetal |
| 5 | Alkoxylation | Glucoside + X—R + Base | Ether |

High molecular weight alkyl glucosides are known to exhibit surface-active properties. However, these amphipathic materials have distinctly different structural features than the intermediate products of the present invention, e.g., their aglycon moiety is hydrophobic, or is a hemiacetal group. This feature is acid sensitive which decreases surfactant performance with time.

It is generally assumed that surfactants composed of similar hydrophilic and lipophilic components possess equivalent surfactant properties. However, structureal differences in methyl glucoside amphiphiles exhibit different surfactant behavior. Hydrophobic attachment at positions other than the aglycon center demonstrate better surface-active properties such as surface and interfacial tension and foam height. Monosubstituted glucoses showed enhanced performance when substituted at the 3-O and 6-O hydroxyl positions.

The present invention employs alkyl glucosides, preferably methyl glucoside, as the hydrophilic moiety. The glucoside radical is a powerful hydrophile due to six hydration sites, i.e., it solubilizes the hydrophobe in water. Methyl glucoside is a non-reducing sugar which is not as susceptible to degradation as the free aldoses. It exists in the cyclic or paranoside form and contains four (4) potentially reactive hydroxyl sites from which various derivatives are available. The pyranose ring remains constant due to the methyl substituted hemiacetal or acetal linkage. As a consequence, surface activity is increased as the interfacial area taken up by a single molecule is larger than if the hemiacetal was unsubstituted.

Preferred non-ionic ether derivatives are those wherein R is lower alkyl and $R_1$ is an alkyl group of 12 to 18 carbon atoms.

Particularly preferred are those ethers of the above formula wherein R is methyl and $R_1$ is dodecyl or octodecyl.

Reactive mesylates are useful reagents for preparing the intermediates of the invention because of their: (1) ease of preparation, (2) synthetic versatility as alkylating agents, (3) high product yield (>80%), and (4) production plant applicability. Also, alkyl mesylates offer the following handling advantages: (1) lower tendency to form emulsions, (2) better crystallizing properties, and (3) high stability against hydrolysis.

Hydrophobic mesylates are readily displaced by nucleophilic metal-glucosides. It appears that alkylation occurs predominantly at the methyl glucosides' primary hydroxyl position. An aprotic solvent (such as DMSO, DMF or THF) facilitates dissolution of the hydrophobe and hydrophile. The mono-valent metal cation is preferably supplied by solid hyroxide pellets ground to a powder and dried under vacuum at ambient temperature for 24 hr. The water by-product of the reaction is removed in-situ by 3 A° molecular sieve which also are ground to a powder and dried under vacuum.

Mechanistically, the reaction proceeds by alcohol addition to a sulfene intermediate. The sulfene is directly derived from mesityl chloride by E2 elimination of hydrogen chloride. Alcoholic nucleophilicity appears to be unimportant.

According to the method of the invention, a 1.OM methyl glucoside solution in DMSO containing solid potassium hydroxide (1 molar equivalent) in the presence of 3 A° molecular sieve was heated to 50° in order to dissolve the sugar under a nitrogen atmosphere. The resulting solution was allowed to reach room temperature. A 1.OM solution of the mesylate in DMSO was added dropwise at room temperature over a 1 hr. period. Then, the reaction mixture was heated to 110° for 24 hr. The reaction's progress was monitored by TLC. After complete methyl glucoside disappearance, the reaction contents were allowed to reach ambient temperature. The sulfonic acid by-products were solubilized in ice-water under vigorous stirring. The hydrophobic glucoside product was extracted from the neutralized aqueous work-up with dichloromethane.

FIGS. 1 and 2 illustrate the foam stablilzation effect for methyl O-docedyl-α-D-glucoside, DMEG, on exemplary shampoo and liquid detergent formulations; respectively. Four (4) different time intervals for each formulation (abscissa) are plotted against the foam height (ordinate). In FIG. 1, sodium laurylsulfonate, SLS, gives a high flash foam initially and then dissipates rapidly at both total surfactant/aqueous (W/V) loading levels of 0.02% and 0.1% (formulations A and C; respectively). SLS's foaming efficacy is increased by DMEG addition at the same loading levels (formulations B and D). Although DMEG decreased the characteristic SLS high flash foam at the higher total surfactant concentration (0.1%, formulations C and D), the foam drainage rate was drastically reduced during the 5 min. period and beyond (13 min.).

Formulation B depicted in FIG. 2 contains a commercial foam stabilizer, Cyclomid DC 212S. The $C_{12}$-nonionic methyl glucoside of the invention stabilized linear alkylbenzenesulfonate, LAS, foam production better than Cyclomid DC 212S by 31% even in the presence of a soil, 100% soybean oil. Both the DMEG/surfactant formulations in FIGS. 1 and 2 gave clear solutions - even in the presence of soybean oil which is water insoluble and acts as a defoamer. Surfactant compatibility is an important formulation criteria for foam stabilizer selection.

EXAMPLE 2

Methyl 6-O-dodecyl-α-glucoside

Methyl α-D-glucoside (7.34 g) and potassium hydroxide (2.12 g) were dissolved in DMSO (40 mL) at 50° in the presence of 3 A molecular sieve under a nitrogen atmosphere for 0.5 h. The heterogeneous brown reaction mixture was allowed to reach room temperature. Dodecyl mesylate (10.00 g) dissolved in DMSO (40 mL) was added dropwise at ambient temperature over a 1.0 h. period. Heating was resumed at 110° until complete methyl glucoside disappearance was indicated by TLC. The reaction contents were allowed to reach room temperature and then poured into an ice-water slurry. This mixture was mixed thoroughly to solubilize the sulfonic acid by-products. The insoluble material was vacuum filtered and the filtrate placed in a separatory funnel. The hydrophobic methyl glucoside product was extracted with dichloromethane. The combined oranic portions were washed with (1) saturated sodium bicarbonate, (2) dried over anhydrous magnesium sulfate, and (3) concentrated on a water-aspirator rotary evaporator. IR and nmr of the syrupy amphiphilic glucoside product were consistent with that of the proposed structure.

Unless indicated otherwise, all percentages expressed herein are by weight.

I claim:

1. A 1-O substituted glucoside having the formula:

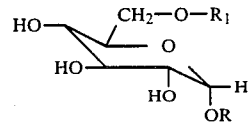

wherein R is selected from the group consisting of an alkyl having 1–20 carbon atoms, phenyl, benzyl and an alkoxyphenol having 1–20 carbon atoms and $R_1$ is an alkyl group from 12 to 18 carbon atoms.

2. A 1-O substituted glucoside according to claim 1 where R is lower alkyl.

3. A 1-O substituted glucoside according to claim 2 wherein R is methyl and $R_1$ is dodecyl.

4. A 1-O substituted glucoside according to claim 2 wherein R is methyl and $R_1$ is octadecyl.

* * * * *